United States Patent
Kanai et al.

(10) Patent No.: US 6,177,544 B1
(45) Date of Patent: Jan. 23, 2001

(54) COLLAGEN-BASED AUXILIARY AGENT FOR OPHTHALMIC SURGERY

(75) Inventors: Atsushi Kanai, 12-14 Komagome 3-chome, Toshima-ku, Tokyo 170-0003; Teruo Miyata, Tokyo; Hiroshi Itoh, Tokyo; Akiko Tanaka, Tokyo, all of (JP)

(73) Assignees: Koken Co Ltd, Tokyo; Japan Science & Technology Corporation, Saitama; Atsushi Kanai, Tokyo, all of (JP)

(*) Notice: Under 35 U.S.C. 154(b), the term of this patent shall be extended for 0 days.

(21) Appl. No.: 09/284,648

(22) PCT Filed: Jun. 11, 1998

(86) PCT No.: PCT/JP98/02578
§ 371 Date: Apr. 16, 1999
§ 102(e) Date: Apr. 16, 1999

(87) PCT Pub. No.: WO99/08636
PCT Pub. Date: Feb. 25, 1999

(30) Foreign Application Priority Data

Aug. 18, 1997 (JP) .................................................. 9-221799

(51) Int. Cl.$^7$ ............................. A61K 38/17; A61K 38/00
(52) U.S. Cl. ............................. 530/356; 530/402; 514/2; 514/21; 514/801; 514/912; 128/DIG. 8
(58) Field of Search .................................. 530/356, 402; 514/2, 21, 801, 912; 128/DIG. 8

(56) References Cited

U.S. PATENT DOCUMENTS

| 4,164,559 | * | 8/1979 | Miyata et al. ........................ 530/356 |
| 4,409,332 | * | 10/1983 | Jefferies et al. ..................... 435/188 |
| 4,851,513 | * | 7/1989 | Devore et al. ........................ 530/356 |

\* cited by examiner

*Primary Examiner*—Christopher S. F. Low
*Assistant Examiner*—Abdel A. Mohamed

(57) ABSTRACT

An auxiliary agent for ophthalmic surgery is based on collagen and, after the completion of surgery, undergoes a lowering in viscosity, and thus can be easily removed. This agent is a neutral solution of collagen which is transparent at a neutral pH and has a denaturation temperature below the intraocular temperature, or a derivative thereof. The agent has a visual light transmission at 400 nm of at least 90% of that before the denaturation, when solution is heated to cause denaturation.

6 Claims, No Drawings

COLLAGEN-BASED AUXILIARY AGENT FOR OPHTHALMIC SURGERY

CROSS-REFERENCE TO RELATED APPLICATION

This application is the Section 371 entry into the United States, based on International PCT application No. PCT/JP98/02578, filed on Jun. 11, 1998.

BACKGROUND OF THE INVENTION

1. Field of the Invention

This invention relates to an ophthalmic surgery auxiliary agent which contains of collagen. In more detail, the invention relates to an ophthalmic surgery auxiliary agent containing collagen whose viscosity drops and becomes easier to remove when the operation is over.

2. Description of the Prior Art

During ophthalmic surgery such as a removing of crystalline lens, a transplant operation of artificial crystalline lens, a trimming at the transplantation of cornea or a transplantation of cornea, when the endothelial cell is hurt, it becomes very difficult to maintain the transparency of the cornea. Therefore, it is very important not to hurt the endothelial cell to maintain the function of cornea after the operation. In general, at the above mentioned ophthalmic surgeries, an ophthalmic surgery auxiliary agent consisting of viscoelastic substance is used for the purpose to protect the cornea. The viscoelastic substance is poured into a camera anterior bulbi as to maintain the depth of camera anterior bulbi, and reduce the possibility of contact of tools to the endothelial cell of cornea and the surrounding tissue, further, the endothelial cell of cornea is protected from the mechanical harm by the adsorption of viscoelastic substances to the endothelial cell of cornea. Obviously, the most important physical feature required to the ophthalmic surgery auxiliary agent is that the material is a higher viscoelastic substance. Furthermore, since the auxiliary agent contacts to the operation part directly, not only the biological safety is required, but also the transparency is necessary not to hinder the view for the operation.

Usually, as the viscoelastic substance, solution of sodium hyaluronate or methyl cellulose are mainly used. Since these substances have a higher viscoelasticity, are superior at the biological safety and have an excellent transparency, they are suitable for the ophthalmic surgery auxiliary agent.

However, the high elasticity which is necessary as the ophthalmic surgery auxiliary agent causes a momentary rising of the intraocular pressure and accompanied with it a breakdown problem of barrier between blood and humor aqueous is caused after the operation, because the viscoelastic substance in camera anterior bulbi disturbs the discharge of aqueous humor which is circulating. Therefore, the procedure to remove the viscoelastic substance from camera anterior bulbi is carried out after the operation, however, because the viscoelasticity of it is too high, it is very difficult to remove it completely. And the problem of intraocular pressure rising certainly occurs after the operation. But the operation auxiliary agent is very useful for the operation and the intraocular pressure rising is only a momentary symptom, the operation auxiliary agent is still extensively used without any improvement.

Meanwhile, the utilization of collagen as the viscoelastic substance have been investigated for a long time. Collagen is a principal protein composing the body of animal, and has an excellent physical property as a biomaterial, which is recognized as a material having a good affinity to the cellular tissue of a living body and can be widely used for the medical device such as a trauma covering material, a hemostatic material and a restoration material for mollis tela recessus portio and so on. And the solution of it has not only a high viscoelasticity which is necessary as the ophthalmic surgery auxiliary agent, but also has a specific feature of collagen whose viscoelasticity can suddenly fall down by heating. That is, because of this special feature, the removal of the operation auxiliary agent after the operation becomes very easy.

However, the natural collagen or the solubilized collagen (aterocollagen) by an enzyme forms fibra in the neutral condition and the solution loses the transparency. Therefore, it is difficult to be used as the starting material of the ophthalmic surgery auxiliary agent which is necessary to have high viscosity and to be transparent. Further, the denaturing temperature of these kinds of collagen is higher than the intraocular temperature 35° C., and since it takes a long time for the denaturation, it is necessary to be removed after the operation in the same manner to the other viscoelastic substance.

To avoid the above mentioned problem, an ophthalmic surgery auxiliary agent composed of a chemically modified collagen not to forming collagen fibra under the neutral condition is proposed. Namely, in the Japanese Patent publication 6-60200, a chemically modified collagen compound containing at least two natural collagen molecules, wherein at least one lysine ε amino group belonging to said collagen molecule is a chemically modified collagen compound bonded by a coupling group, said coupling group containing at least two parts selected from carbonyl and sulfonyl group, further said chemically modified collagen compound being soluble in a physiological buffer solution, is disclosed.

However, when said auxiliary agent is adopted for use in the eye which is a very sensitive organ, the safety of the coupling agent is a problem. Further, since by the intermolecular bonding, the lowering of viscoelasticity is controlled, it becomes necessary to be removed after the operation.

Further, in the Japanese patent application 53-49610, a succinylized collagen is disclosed as a chemically modified collagen which does not form fibra in neutral condition, and in the Japanese patent application 42-59201 a collagen solubilized by alkali is disclosed. These collagens do not form fibra and keep transparency in neutral condition, and since the denature temperature is lower than the intraocular temperature, viscoelasticity falls down quickly after the operation and is easy to be removed.

When an actual operation test is carried out on animal's eye using said disclosed substance as an auxiliary agent, the generation of white muddy substance is observed at the denaturing by the intraocular temperature. Accordingly, these substances are not desirable ones as the auxiliary agent. Namely, the maintenance of view for the operation is deteriorated, further, during the observation term after the operation, it becomes very difficult to distinguish the white muddy substance from an intraocular inflammation. Therefore, there is a possibility of a wrong diagnosis. Further, when the white muddy substance remains, it has a possibility of raising the intraocular pressure.

DISCLOSURE OF THE INVENTION

The inventors of this invention have conducted intensive study about the ophthalmic surgery auxiliary agent in order to solve the above mentioned problems, and accomplished the present invention. That is, the inventors have developed the ophthalmic surgery auxiliary agent which does not form fibra in neutral condition and maintains transparency, and the viscosity falls down when it is removed after the operation. The object of this invention is to provide an ophthalmic surgery auxiliary agent comprising a collagen solution which can keep its transparency before and after the operation, does not form white muddy substance by denaturation, and can easily be removed because the viscosity of it falls lown after the operation.

The important point of this invention is that, an ophthalmic surgery auxiliary agent composed of collagen or a neutral solution of collagen derivative which is transparent under neutral conditions and has a lower denaturation temperature than the intraocular temperature, whose transmissivity to 400 nm visible radiation after denaturation by heat is bigger than 90% of the transmissiving before denaturation. The isoionic point of said ophthalmic surgery auxiliary agent is desirably smaller than 6. The collagen whose side chain is chemically modified can be used as a collagen derivative, further, the collagen derivative is desirably an alkali solubilized collagen.

That is, the present invention provides an ophthalmic surgery auxiliary agent whose starting material is collagen alone, and during the operation since the auxiliary agent has a proper viscosity, it has a protection effect to the cornea endotheliocytus and after the operation the viscosity falls dawn and is easily removed. Further, after the auxiliary agent is denatured and viscosity falls down, it can keep a good transparency. Since the material of this auxiliary agent is only a collagen, it does not exert bad influences to eyes such as an intraocular inflammation. And, since the material does not form white muddy substance after denaturation, it can keep its transparency after the operation and does not raise the intraocular pressure.

THE BEST EMBODIMENT TO CARRY OUT THE INVENTION

The present invention will be illustrated more fully by the following description.

The starting material of collagen which is used in this invention is desirably a body structure such as skin or tendo calcaneus obtained from mammals e.g. cow, pig and horse, however, it is not intended to be limited to them, and any collagen whose isoionic point is bigger than 6 can be used. Concretely, alkali solubilized collagen or acylated collagen such as succinylated, phthalated, and acetylated collagen can be used. And, as the collagen to be acylated, there may be mentioned, without limitation, acid solubilized collagen, salt solubilized collagen, enzyme solubilized collagen (aterocollagen) and alkali solubilized collagen.

It is possible to improve the transparency of the operation auxiliary agent of this invention and its transparency after denaturation, by restricting the content of lipid to the lower level. Concretely, a material skin structure is washed by organic solvent as to remove lipid. Further, the sediment of collagen before dissolving is washed well by water and refining carefully the obtained collagen. Thus the collagen of lower lipid content can be obtained.

The acid solution of collagen is filtered as to remove not only high molecular compound but also the substance which causes white muddiness, whereby transparency of the prepared collagen is improved, and further the transparency can be maintained after the denaturation. In this invention, a membrane filter smaller than 0.45 $\mu$m is used for the filtration. At the filtration procedure, when the collagen solution is pressed too much, the high molecular compound and the substance which causes white muddiness can pass through the filter. Therefore, the higher filtering condition than necessary level should be avoided, and in a case of collagen content in collagen solution of lower than 20 mg/mL, the desirable filtering pressure of lower than 4 atm.

To denature the operation auxiliary agent of this invention and to reduce the viscoelasticity of it after the operation, it is necessary that the collagen is a collagen which has a denaturing temperature lower than the intraocular temperature. Namely, desirably the denaturing temperature of collagen is to be lower than 35° C. Since the denaturing temperature of collagen depends on its isoionic point, the denaturing temperature can be controlled by altering the isoionic point. Acid solubilized collagen, salt solubilized collagen and acylated compound of aterocollagen can adjust the isoionic point to smaller than 6 by making acylating degree higher, and any of these can be used as an operation auxiliary agent. Acylation can be carried out by ordinary method, and when the acylation ratio is 50%, the denaturing temperature becomes 35° C. and the isoionic point becomes smaller than 6. And, since the isoionic point of an unmodified alkali solubilized collagen is about 5.0, it can be used as is, however, the isotonic point can be reduced lower than 5 by the further acylation.

In a case of alkali solubilized collagen, under the condition of temperature rising rate 7 minutes/° C., the denaturing temperature is about 34° C. Meanwhile, in a case of succinylated aterocollagen of 4.5 isoionic point, by denaturing under the same condition, the denaturing temperature is about 32° C. Therefore, the denaturing temperature can be regulated by altering the acylation ratio.

Collagen can be regulated to the neutral solution having same penetration pressure to the living body and can be used. Concretely, a collagen solution dissolved in physiological saline solution or in phosphoric acid buffer solution is prepared. The concentration of collagen is in the range from 5 mg/mL to 30 mg/mL, and preferably from 10 mg/mL to 20 mg/mL.

When said neutral collagen solution is heated to 35° C., which is the intraocular temperature, it denatures. In this case, when the transmissivity to 400 nm visible radiation before and after denaturation is taken into consideration, it is necessary that the transmissivity does not deteriorate to smaller than 90%, desirably 95%, by the denaturation. When it is deteriorated to smaller than 90%, the maintenance of view for the operation becomes difficult and there is a possibility that the intraocular pressure will rise after the operation.

EXAMPLES

The present invention will be understood more readily with reference to the following Examples, however, the examples are not intended to limit the scope of the invention.

Example 1

A specimen of cow skin is soaked in 70% of ethanol for one week and lipid is removed, and dissolved in alkaline solution (0.75N sodium hydroxide, sodium sulfate and monomethyl amine) for 2 weeks. Then said specimen of cow skin is washed in neutral solution, recycled by centrifuge for several times and the sediment of collagen is obtained. pH of the solution is adjusted to 2.5 as to dissolve the sediment, then collagen concentration is adjusted to 0.5%. The obtained solution is filtered at 4 atm by a pressure filter housing product of Zaltrius Co., Ltd.). The obtained solution is concentrated and there is prepared a neutral solution of 1.5% collagen concentration (0.1M phosphoric acid buffer solution). The isolonic point of said obtained alkali solubilized collagen is 4.95, and the denaturing temperature is 34.1° C.

The obtained solution is heated to 35° C., and no white muddy substance is observed, and the good transparency is maintained and the transmissivity after denaturation is over than 95% compared to that of before denaturation.

Example 2

A specimen of cow skin is soaked in 70% of ethanol for two days and lipid, is removed, and dissolved in alkaline solution (1.0N sodium hydroxide, sodium sulfate and monomethyl amine) for 1 week. Then said specimen of cow skin is washed in neutral solution, recycled by centrifuge for several times and the sediment of collagen is obtained. pH of the solution is adjusted to 2.5 to dissolve the sediment, then collagen concentration is adjusted to 0.5%. The obtained solution is filtered at 4 atm by a pressure filter housing. The obtained solution is concentrated and there is prepared a neutral solution of 1.5% collagen concentration (0.1M phosphoric acid buffer solution).

0.2 ml of the obtained solution is put into a camera anterior bulbi of rabbit and the condition of the solution was observed for 24 hours. The white muddy substance did not generate and the intraocular pressure did not rise, further, the transparent camera anterior bulbi, like that of normal eye, was maintained.

Example 3

A pepsin solubilized collagen is prepared by well known method. pH of 100 ml of this collagen solution is adjusted to 9 and collagen dispersion is generated. 0.1 ml of 1% succinic acid acetone anhydride is added to the dispersion and stirred for 3 hours maintaining pH 9, then succinic acid is removed by dialysis to water, and succinylated aterocollagen is obtained. The obtained collagen is dissolved at pH 2.5 and is filtered under an by atmosphere lower than 4 atm by a pressure filter housing at 0.5% collagen concentration. The obtained solution is concentrated and a neutral solution of collagen, concentration 1.5% (0.1M phosphoric acid buffer solution), is prepared. The isoionic point of this succinylated collagen is 4.46 and the denaturing temperature is 31.9° C.

The obtained solution is heated to 35° C., and no white muddy substance is observed, and the good transparency is maintained and the transmissivity after denaturation is over than 95% compared to that of before denaturation.

COMPARATIVE EXAMPLE

The material cow skin is washed by water and dissolved in alkaline solution (0.75N sodium hydroxide, sodium sulfate and monomethyl amine) for 2 weeks. Then said specimen of cow skin is washed in neutral solution, recycled by centrifuge for several times and the sediment of collagen is obtained. pH of the solution is adjusted to 2.5 to dissolve the sediment, then collagen concentration is adjusted to 0.75%. The obtained solution is filtered at 5 atm by a pressure filter housing. The obtained solution is concentrated and a neutral solution of collagen, concentration 1.5% (0.1M phosphoric acid buffer solution), is prepared.

0.2 ml of the obtained solution is put into a camera anterior bulbi of rabbit and the conditions were observed for 24 hours. The intraocular pressure began to rise and the generation of white muddy substance was observed after 4 hours, and the intraocular pressure and the generation of white muddy substance showed a peak value after 6 hours. After 24 hours, the white muddy substance disappeared and the intraocular pressure became normal value.

POSSIBILITY FOR THE INDUSTRIAL USE

As mentioned above, the ophthalmic surgery auxiliary agent comprising collagen of this invention, has a high viscoelasticity effective to protect the surrounding living organization at the operation, and after the operation it denatures quickly and the viscoelasticity remarkably falls down. Further, the collagen of this invention does not generate white muddy substance after the denaturation and can maintain the transparency before and after the operation. Therefore, the problem of the intraocular pressure rising which is common in the conventional auxiliary agent is not observed in this auxiliary agent and does not disturb the diagnosis of a medical doctor after the operation. The auxiliary agent of this invention can be used safely.

What is claimed is:

1. An ophthalmic surgery auxiliary agent consisting essentially of non-fibrous collagen selected from the group consisting of alkali solubilized collagen or acylated collagen, in a neutral pH solution, said agent (i) being transparent at neutral pH;

(ii) having a denaturation temperature below 35° C.; and (iii) having a transmissivity to 400 nm visible radiation, after denaturation by heat, larger than 90% of the transmissivity before denaturation.

2. The ophthalmic surgery auxiliary agent of claim 1, wherein said collagen has an isoionic point of less than 6.

3. The ophthalmic surgery auxiliary agent of claim 1, wherein said collagen has a chemically modified side chain amino group.

4. The ophthalmic surgery auxiliary agent of claim 1, wherein the collagen comprises alkali solubilized collagen.

5. The ophthalmic surgery auxiliary agent of claim 1, wherein the collagen comprises acylated collagen.

6. The ophthalmic surgery auxiliary agent of claim 5, wherein the acylated collgen comprises succinylated collagen.

* * * * *